United States Patent
Agrawal

(10) Patent No.: US 8,960,432 B2
(45) Date of Patent: Feb. 24, 2015

(54) MEDICAL DEVICE PACKAGING SYSTEM, PACKAGE AND METHOD

(71) Applicant: Cook Medical Technologies LLC, Bloomington, IN (US)

(72) Inventor: Sony Agrawal, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/150,240

(22) Filed: Jan. 8, 2014

(65) Prior Publication Data

US 2014/0305827 A1 Oct. 16, 2014

Related U.S. Application Data

(60) Provisional application No. 61/810,298, filed on Apr. 10, 2013.

(51) Int. Cl.
*B65B 63/04* (2006.01)
*A61B 19/02* (2006.01)
*B65H 55/02* (2006.01)

(52) U.S. Cl.
CPC ............... *A61B 19/026* (2013.01); *B65B 63/04* (2013.01); *B65H 55/02* (2013.01)
USPC ............................. 206/438; 206/364; 206/489

(58) Field of Classification Search
USPC .................. 206/438, 364, 489; 211/85.13
See application file for complete search history.

(56) References Cited

U.S. PATENT DOCUMENTS

| | | | | |
|---|---|---|---|---|
| 3,206,014 | A | * | 9/1965 | Blumberg ....................... 206/6.1 |
| 3,633,758 | A | * | 1/1972 | Morse et al. ................ 211/85.13 |
| 4,262,800 | A | * | 4/1981 | Nethercutt ..................... 206/364 |
| 4,923,061 | A | | 5/1990 | Trombley, III |
| 5,105,942 | A | * | 4/1992 | van Veen et al. .............. 206/364 |
| 5,344,011 | A | | 9/1994 | DiBernardo et al. |
| 5,526,928 | A | * | 6/1996 | Yabe et al. ..................... 206/364 |
| 6,047,825 | A | | 4/2000 | Samuels |
| 6,405,414 | B1 | | 6/2002 | Byrnes et al. |
| 6,588,588 | B2 | | 7/2003 | Samuels |
| 6,719,135 | B2 | | 4/2004 | Armijo |
| 6,902,057 | B2 | * | 6/2005 | Duffy ............................. 206/364 |
| 7,461,741 | B2 | | 12/2008 | State et al. |
| 7,886,906 | B1 | | 2/2011 | Dunn |
| 2005/0178684 | A1 | * | 8/2005 | Kesler et al. .................. 206/364 |
| 2008/0006554 | A1 | * | 1/2008 | Duffy et al. ................... 206/438 |
| 2011/0127186 | A1 | * | 6/2011 | Enns et al. ..................... 206/364 |

* cited by examiner

*Primary Examiner* — Steven A. Reynolds
*Assistant Examiner* — King M Chu
(74) *Attorney, Agent, or Firm* — Liell & McNeil

(57) ABSTRACT

A packaging system for medical devices includes a elongate connector having a plurality of channels formed therein, and a first and a second tubular holder configured to form an assembly with an elongate, coiled medical device. The first and second tubular holders each have shapes congruous with the plurality of channels, and are positionable therein such that the elongate connector forms a bridge attaching the tubular holders in an assembly with a medical device.

20 Claims, 4 Drawing Sheets

MEDICAL DEVICE PACKAGING SYSTEM, PACKAGE AND METHOD

TECHNICAL FIELD

The present disclosure relates generally to the field of medical device packaging, and relates more particularly to a packaging system accommodating elongate medical devices having a range of lengths and stiffnesses.

BACKGROUND

A great many different medical device packaging strategies and systems have been proposed over the years. Considerations such as simplicity and efficiency of device placement within a package, protection of device features in storage or during shipping, and unpackaging of a medical device for use are all factors which can drive package design. Many medical devices, for instance, are produced at relatively high volume, but must be independently packaged, often manually, thus placing a premium on the speed at which a technician can load such devices. Many medical devices also have relatively fragile or sensitive mechanical or material features which need to be protected from damage or alteration during the packaging process, shipping and storage, and removal from a package. In some instances, the package itself or parts of the package are configured to assist a clinician in deploying a medical device for use within a patient. In view of the above considerations, many sophisticated packaging systems are now in widespread use and serve functional considerations along the entire continuum from production to end use.

Certain classes of medical devices can have features which, while generally analogous, are sufficiently dissimilar as to justify independent package designs even for seemingly similar devices. One example of this is known from the technical area of wire guides. Many wire guides outwardly appear to be a simple elongate metallic wire, but upon closer examination have varying properties such as stiffness, coating, or microscopic construction. Wire guides can be relatively sensitive to bending and deformation, and are therefore often packaged either substantially elongated, or in the form of a coil. For wire guides having a range of stiffnesses, and other properties such as differing lengths and shape memory properties, purpose built packaging systems are often used for each separate type of wire guide. As a result, manufacturers, packagers or assemblers are often required to keep on hand a relatively large inventory of wire guide packaging systems.

U.S. Pat. No. 3,633,758 to Morse is directed to a catheter storage rack, having a rigid supporting plate upon which spaced tubular guides are mounted and arranged based upon a desired configuration of a catheter to be supported on the rack. Morse is apparently adapted to retain and support an end of the catheter in a "naturally" curved configuration. While Morse may be adequate for its intended purpose, it would appear that the design requires a relatively large amount of material, and may have other drawbacks.

SUMMARY OF THE DISCLOSURE

In one aspect, a packaging system for medical devices includes an elongate connector having a first and a second longitudinal end, and defining a latitudinal centerline located between the first and second longitudinal ends. The elongate connector further includes a lower surface, and an upper surface having a plurality of channels formed therein. The plurality of channels includes a first set of longitudinally spaced channels located on a first side of the latitudinal centerline, and a second set of longitudinally spaced channels located on a second side of the latitudinal centerline. The packaging system further includes a first and a second tubular holder configured to form an assembly with an elongate medical device held in a coiled configuration by the first and second tubular holders opposed by an internal bias of the elongate medical device tending to uncoil the same. The first and second tubular holders each have shapes congruous with shapes of the plurality of channels, and being positionable within any combination of one of the first set of longitudinally spaced channels and one of the second set of longitudinally spaced channels, such that the elongate connector forms a bridge attaching the first and second tubular holders in the assembly with the elongate medical device.

In another aspect, a medical device package includes an elongate connector having a first and a second longitudinal end, a lower side, and an upper side having formed therein a first and a second channel positioned upon opposite sides of a latitudinal centerline located between the first and second longitudinal ends. The package further includes a first and second tubular holder, and an elongate medical device held in a coiled configuration by the first and second tubular holders in opposition to an internal bias of the elongate medical device tending to uncoil the same. The first and second tubular holders are positioned within the first and second channels, respectively, such that the elongate connector forms a bridge attaching the first and second tubular holders.

In still another aspect, a method of packaging an elongate medical device includes coiling an elongate medical device against an internal bias of the elongate medical device tending to uncoil the same. The method further includes feeding the elongate medical device through a first and a second tubular holder during the step of coiling, such that the first and second tubular holders form an assembly with the elongate medical device in a coiled configuration opposed by the internal bias. The method further includes positioning the first and second tubular holders within a first and a second channel, respectively, located upon opposite sides of a latitudinal centerline in an elongate connector, such that the elongate connector forms a bridge attaching the first and second tubular holders in the assembly with the elongate medical device.

DETAILED DESCRIPTION

Figure 1:
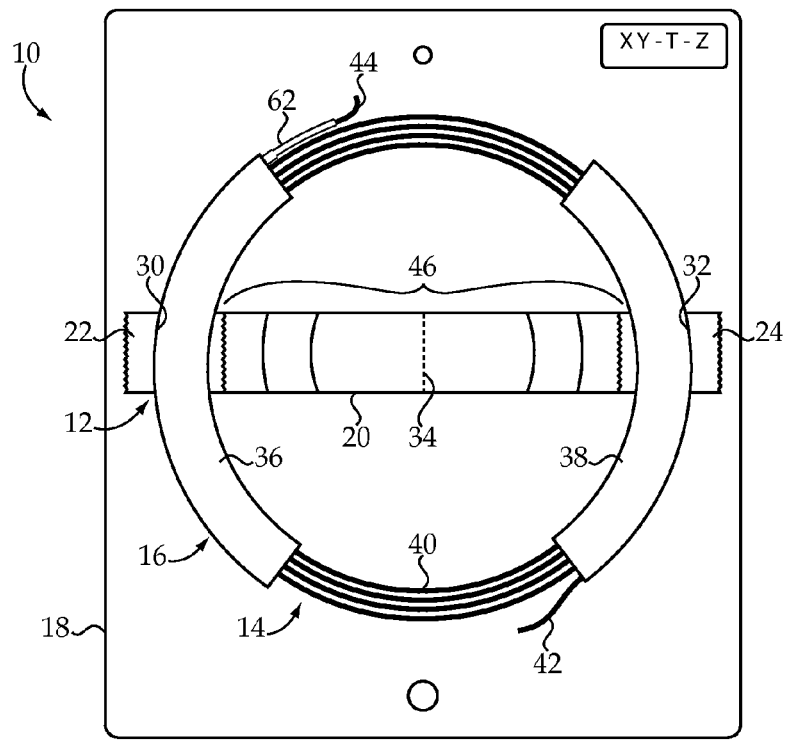
FIG. 1 is a diagrammatic view of a medical device package, according to one embodiment.

Referring to FIG. 1, there is shown a medical device package 10 according to one embodiment. Package 10 includes a packaging system 12 forming an assembly 16 with an elongate medical device 14. Assembly 16 may be positioned within a sterile, peel-open pouch 18 of system 12 in certain embodiments. Pouch 18 may be configured for sterilization of assembly 16, and storage and shipping in a conventional manner. In the illustrated embodiment, medical device 14 includes a wire guide having an elongate body 40 with a proximal end 42 and a distal end 44. Device 40 may have a substantially uniform stiffness apart from distal end 44, which may be relatively soft or floppy in certain embodiments. Device 40 could nevertheless have any stiffness or stiffness profile, and instead of a wire guide could also be a catheter, sheath or the like. As will be further apparent from the following description, packaging system 12 is contemplated to be easy to use, rapidly assembled, and readily unpackaged for service of device 40. As also further discussed herein, packaging system 12 is contemplated to be advantageously used with elongate medical devices having a range of lengths and stiffnesses, each having different packaging specifications, and is conservative in its use of packaging material.

Packaging system 12 may include an elongate connector 20 having a first longitudinal end 22 and a second longitudinal end 24. Connector 20 further includes a lower side, not visible in FIG. 1, and an upper side 28 having formed therein a first channel 30 and a second channel 32. First and second channels 30 and 32 are positioned upon opposite sides of a latitudinal centerline 34 located between first and second ends 22 and 24. System 12 may further include a first tubular holder 36 and a second tubular holder 38. Device 14 is held in a coiled configuration by first and second holders 36 and 38 in opposition to an internal bias of device 14 tending to uncoil the same. It will thus be understand that holders 36 and 38 maintain device 14 in the coiled configuration, and device 14 would otherwise tend to assume a different configuration but for the constraint of holders 36 and 38. The "other" configuration of device 14 might be a linear configuration, but the present disclosure is not thusly limited.

First and second holders 36 and 38 are positioned within first and second channels 30 and 32, respectively, such that connector 20 forms a bridge 46 attaching first and second holders 36 and 38. In the illustrated embodiment, bridge 46 may be understood as that part of connector 20 spanning the clearance between holders 36 and 38. By way of bridge 46, connector 20 assists in maintaining holders 36 and 38 with device 14 coiled therein in a configuration suitable for storage, shipping and handling during eventual unpackaging and deployment. Thus, while frictional interaction between device 14 and holders 36 and 38 may tend to prevent device 14 from slipping out of its coiled configuration and partially or totally out of one or both of holders 36 and 38, connector 20 assists in maintaining the general coiled and packaged configuration depicted in FIG. 1, and can further be used by an assembler or clinician for holding and/or manipulation of assembly 16 for purposes which will be apparent to those skilled in the art. Distal end 44 and proximal end 42 protrude from holders 38 and 36, respectively, and an end protector 62 is positioned upon distal end 44 in the FIG. 1 illustration.

Figure 2:
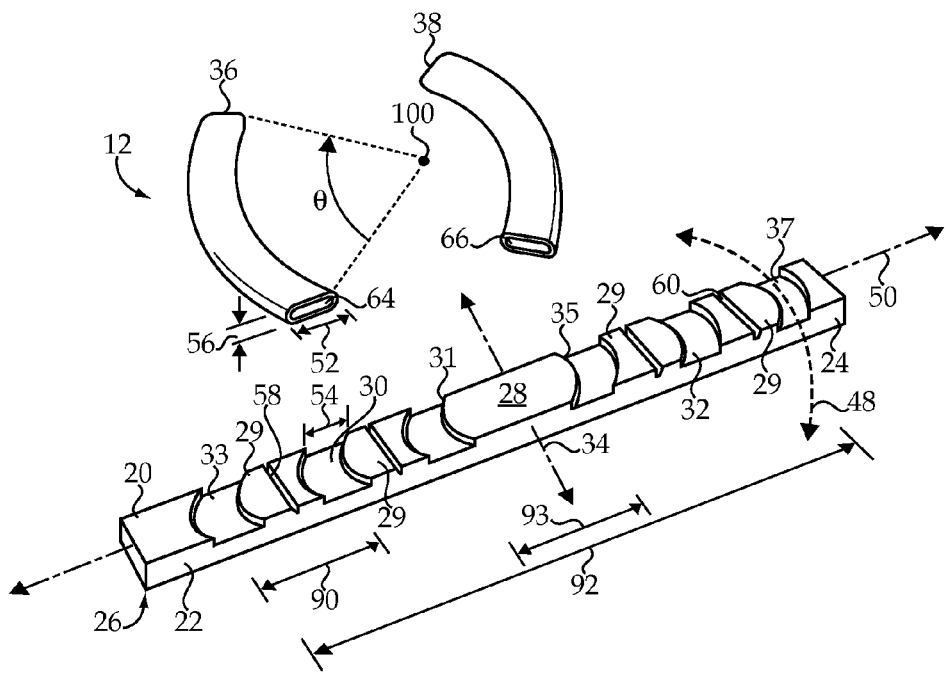
FIG. 2 is a perspective view of a disassembled medical device packaging system, according to one embodiment.

Referring also now to FIG. 2, there is shown packaging system 12 disassembled, and prior to assembly with device 14. Reference numeral 26 identifies generally lower surface 26 of connector 20, opposite upper surface 28. As mentioned above, a first channel 30 and a second channel 32 may be formed in upper surface 28. In a practical implementation strategy, first and second channels 30 and 32 may be part of a plurality of channels formed in upper surface 28, and including a first set of longitudinally spaced channels, including channel 30, another channel 31 positioned inboard of channel 30, and yet another channel 33 positioned outboard of channel 30. The plurality of channels may further include a second set of longitudinally spaced channels including channel 32, another inboard channel 35 and another outboard channel 37. In a practical implementation strategy, the first set of longitudinally spaced channels 30, 31 and 33 each have a first channel shape, and the second set of longitudinally spaced channels 32, 35 and 37 each have a second channel shape substantially a mirror image of the first channel shape, as shown in FIG. 2.

In a further practical implementation strategy, each of the first and second channel shapes includes an arcuate channel shape. The arcuate channel shapes, which may be substantially identical among all of the plurality of channels but for the mirror image aspect, may each define a circular arc 48 opening toward latitudinal centerline 34. Accordingly, each of channels 30, 31 and 33 would fairly be understood to have an arcuate shape defining a circular arc opening toward centerline 34, whereas the same can be said for channels 32, 35 and 37. Connector 20 may further define a longitudinal axis 50 bisecting each of the circular arcs 48 in a projection plane. Longitudinal axis 50 can be understood as a geometric center axis extending between first and second ends 22 and 24, approximately half-way between surfaces 26 and 28. Circular arc 48 would thus be understood to be positioned out of plane with axis 50, but in a projection plane bisected by axis 50. When holders 36 and 38 are assembled with connector 20 they too may be understood as bisected by axis 50 in a projection plane. Lower surface 26 may be substantially planar, but could alternatively be contoured similarly with upper surface 28, or have some other shape or contour. Upper surface 28 may further include a plurality of substantially coplanar land areas 29 each extending between adjacent ones of the plurality of channels.

Additional features shown in FIG. 2 include a first break line 58 located between channel 30 and channel 33, and a second break line 60 located between channel 32 and channel 37. Additional break lines (not numbered) may be located between channel 30 and 31 and channels 32 and 35, for reasons which will be further apparent from the following description. Connector 20 may be formed of a material such as an elastomeric material suitable for injection molding or another suitable molding technique. Each of first and second break lines 58 and 60 may be formed by at least one of, a non-uniformity in a thickness of the material, such as might be created via scoring connector 20, and a void in the material such as might be formed by perforating connector 20. Rather than post-molding techniques, "scoring" or "perforating" of connector 20 might be achieved via molding-in features appropriate and suitable for such purposes. In any event, break lines 58 and 60 can provide a visual cue to a technician for breaking or cutting connector 20 at suitable locations for purposes discussed herein, and can additionally or alternatively provide a zone of relative weakness to facilitate snapping-off pieces from connector 20.

In FIG. 2, holders 36 and 38 are shown as they might appear prior to positioning within channels 30 and 32, respectively. It may be noted that each of holders 36 and 38 has a shape congruous with shapes of all the plurality of channels formed in upper surface 28. Accordingly, either of first and second holders 36 and 38 could be positioned within any one of the plurality of channels. More particularly, holders 36 and 38 may be positionable within any combination of one of the first set of longitudinally spaced channels 30, 31, 33 and one of the second set of longitudinally spaced 32, 35, 37, such that connector 20 forms bridge 46 attaching holders 36 and 38 in assembly 16. It will thus be appreciated that, rather than channels 30 and 32, holders 36 and 38 might be positioned within channel 31 and channel 35, channel 31 and channel 37, channel 32 and channel 30 as shown in FIG. 1, or any other combination of one of the first set and one of the second set of longitudinally spaced channels. This capability enables the advantageous flexibility of use of system 12 for packaging elongate medical devices having a range of lengths and stiffnesses as noted above.

For instance, a relatively short and relatively flexible wire guide could form an assembly with holders 36 and 38 when positioned within channels 31 and 35. For a medical device of similar length but greater stiffness, holders 36 and 38 might be positioned within channels 30 and 32, potentially within channels 30 and 35, or some other combination of channels having a greater longitudinal spacing between them to account for the relatively greater stiffness. An elongate medical device that is both relatively long and relatively stiff could be packaged as contemplated herein via positioning holders 36 and 38 in channels 33 and 37, respectively. While the embodiment shown includes a total of six channels, three on each side of latitudinal centerline 34, other embodiments could include a greater number of channels, such as four, five, six or more channels on each side of centerline 34, or a lesser number such as a total of two channels on each side of centerline 34. In any event, a total of at least four channels, having among them at least two different longitudinal spacings across centerline 34, will typically be used.

Positioning of holders 36 and 38 within whichever ones of the plurality of channels are selected can include interference fitting holders 36 and 38 therein. As noted above, holders 36 and 38 may be congruous with each of the plurality of channels. Accordingly, each of holders 36 and 38 may have an arcuate holder shape. The arcuate holder shape may include a partially circular shape, such that each of holders 36 and 38 defines an arc segment of a circle, generally analogous to arc segment 48. In FIG. 2, a center point 100 of a circle defined by holder 36 is shown, and an arc angle Θ defined by holder 36. Angle Θ might be from about 30° to about 120°, in certain embodiments. Holder 36 may have a greater radial thickness 52, in relation to the circle having center point 100, and each of the plurality of channels may have a lesser radial thickness 54, in relation to an analogously defined circle such as that which would be defined by arc segment 48. Upon positioning holder 36 within channel 30, holder 36 or connector 20 can be deformed such that holder 36 is positioned and retained within channel 30 via an interference fit. An assembler can thus "snap in" holder 36 into channel 30, and could analogously do the same within any other combination of holders 36 or 38 and any of the plurality of channels formed in upper surface 28 of connector 20. In addition to radial thickness 54 being less than radial thickness 52, either or both of the plurality of channels and holders 36 and 38 could be shaped to facilitate or enhance interference fitting. For instance, channel 30, or any of the other plurality of channels, could be relatively wider in a longitudinal direction at a bottom of the channel relatively closer to lower surface 26, and narrower in a longitudinal direction at a top of the channel substantially aligned with the adjacent lands 29. It may also be noted that first and second holders 36 and 38 each define a through passage 64 and 66, respectively, for receipt of the elongate medical device fed therethrough. Moreover, each of holders 36 and 38 may have the form of a flattened tube, where an axial thickness 56 shown in connection with holder 36 is less than radial thickness 52. The generally flattened shape of holders 36 and 38, in conjunction with a generally flat bottom contour of the channels formed in upper surface 28, can assist in maintaining holders 36 and 38 within the selected channels, and also help keep the profile of package 10 relatively thin.

Also shown in FIG. 2 is a first longitudinal dimension 90 which illustrates an approximate center to center distance between channels 33 and 30. In a practical implementation strategy, distance 90 may be from about 0.5 inches to about 2 inches. A longitudinal spacing between adjacent channels in the first set and between adjacent channels in the second set may be substantially uniform. Also shown in FIG. 2 is another longitudinal dimension 92 representing an inner diameter dimension between channel 33 and channel 37, and a third dimension 93 representing an analogous inner diameter dimension between channel 31 and channel 35. In a practical implementation strategy, dimension 92 may be from about 6 inches to about 10 inches, and dimension 93 may be from about 3 inches to about 5 inches. As used herein, the term "about" should be understood in the context of conventional rounding to a consistent number of significant digits. Accordingly, "about 6 inches" means from 5.5 inches to 6.4 inches, and so on.

INDUSTRIAL APPLICABILITY

Figure 3:
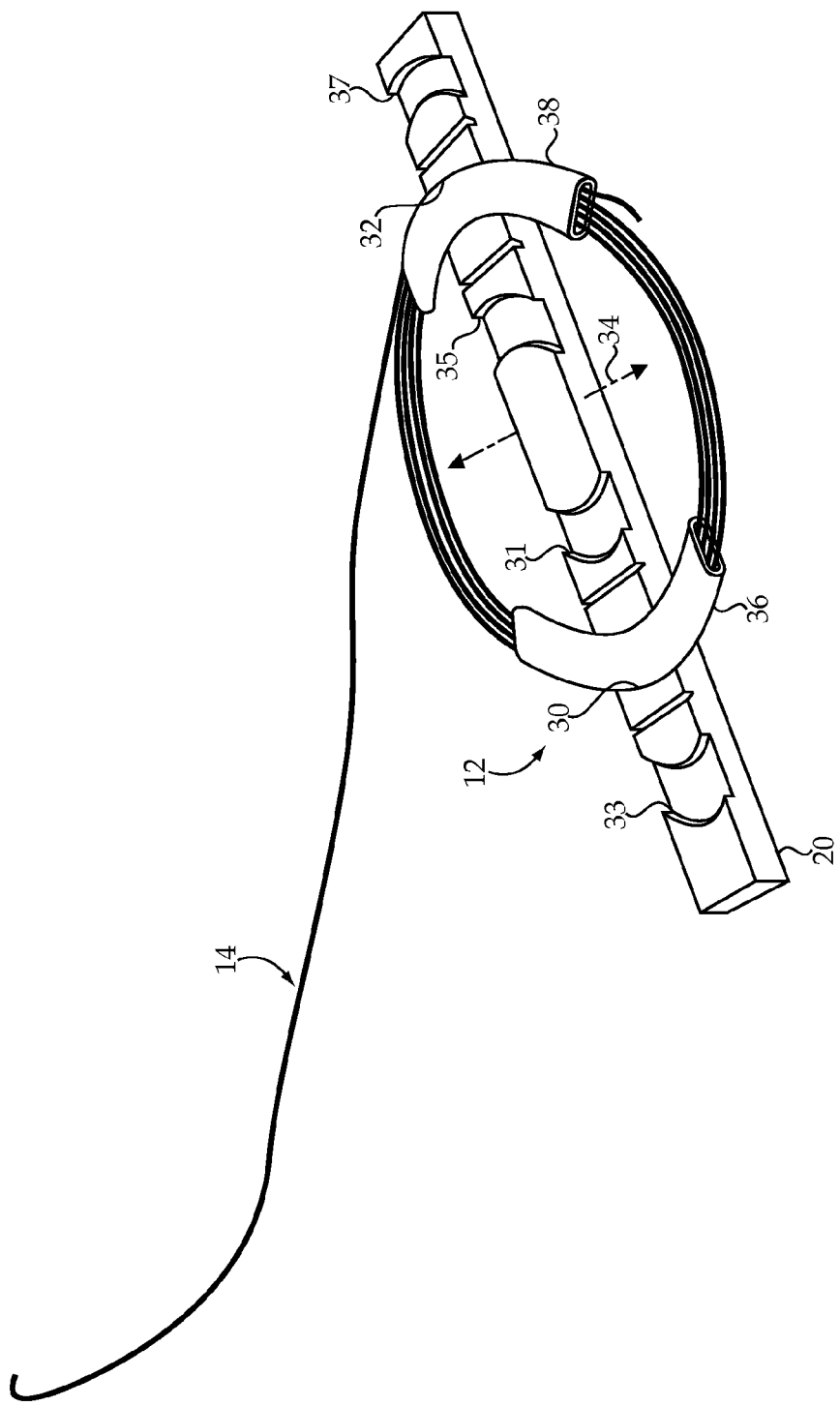
FIG. 3 is a perspective view of the packaging system at one stage of assembly with a medical device.

Referring now to FIG. 3, there is shown device 14 having been coiled against its internal bias tending to uncoil device 14, while being fed through holders 36 and 38. In FIG. 3, device 14 is depicted in the process of forming an assembly with holders 36 and 38, and also with connector 20. In a practical implementation strategy, holders 36 and 38 may be positioned within channels 30 and 32 respectively, or any other suitable combination of the channels, prior to feeding medical device 14 through holders 36 and 38. In other embodiments, device 14 could be coiled and fed through holders 36 and 38 as described herein prior to positioning holders 36 and 38 within the corresponding channels.

As noted above, elongate medical devices such as wire guides may have a specified packaging configuration, such as a specified diameter or range of diameters for the medical device in a coiled configuration. According to the present disclosure, first and second holders 36 and 38 may be positioned within the respective channels such that a clearance between holders 36 and 38 is matched to a longitudinal spacing between the selected channels, on the basis of a predefined specification. Accordingly, one can readily envision an assembler receiving a wire guide for packaging, looking up a specified diameter of that wire guide once placed in its coiled configuration, and then selecting suitable channels in connector 20 for placement of holders 36 and 38.

Figure 4:
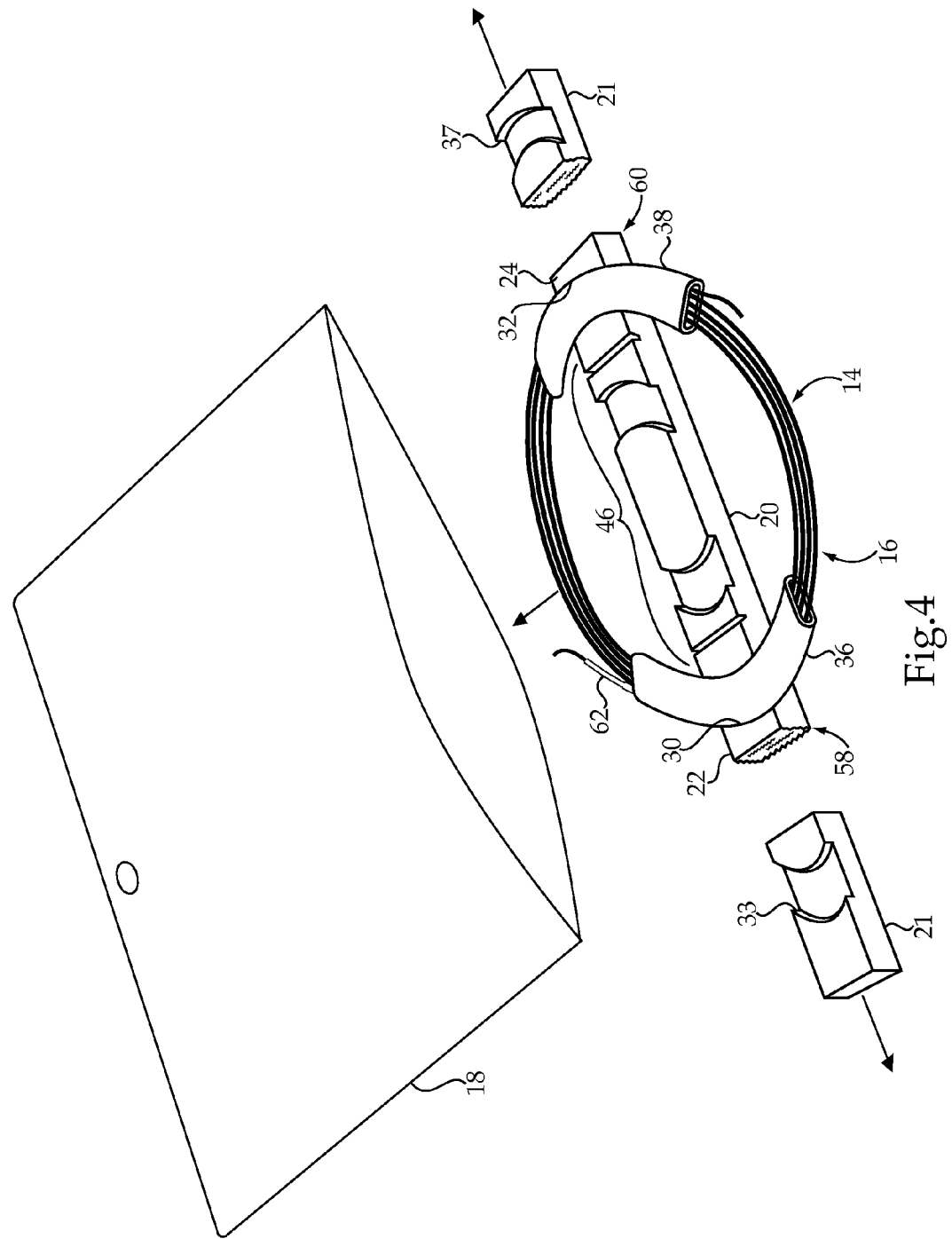
FIG. 4 is another perspective view of the system of FIG. 3, at another stage of assembly with a medical device.

Referring now to FIG. 4, there is shown device 14 having formed assembly 16 with holders 36 and 38, which are positioned within selected channels in connector 20. It will be recalled that connector 20 can be equipped with break lines 58 and 60. In FIG. 4, end pieces 21, formerly forming longitudinal ends 22 and 24 of connector 20 have been broken off or otherwise detached from the main portion of connector 20 forming bridge 46 to attach holders 36 and 38. Detached pieces 21 can be discarded or recycled. In the case that holders 36 and 38 are fitted into different channels, different end pieces might be broken off, or none at all. As alluded to above, the present packaging strategy, and notably component shapes, enables a relatively low profile or thin medical device package. The ability to snap off unused material further enables the width of the medical device package to also be made relatively smaller than what might otherwise be required. With end pieces 21 detached, and device 14 formed into assembly 16, assembly 16 can be inserted into pouch 18, and the resulting package forwarded for sterilization, shipping, storage, etc.

Figure 5:
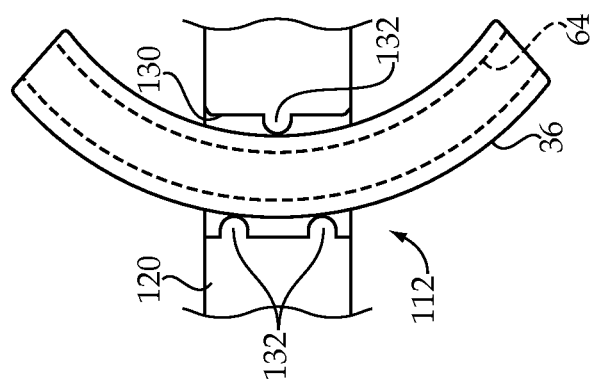
FIG. 5 is a top elevational view of a portion of a packaging system, according to another embodiment.

Referring to FIG. 5, it will be recalled that the holders contemplated herein will typically be congruous with a shape of the channels in the connector within which the holders are received. FIG. 5 sets forth an alternative embodiment of a packing system 112, where a connector 120 has a channel 130 formed therein which, rather than having an arcuate shape, forms a plurality of protrusions, extending inwardly into the channel and configured to retain holder 36 therein. Despite holder 36 having an arcuate shape, and channel 130 not having an arcuate shape, the respective shapes can still fairly be considered congruous. In a manner generally analogous to that described with the foregoing embodiments, holder 36 can be interference fitted into channel 130, deforming protrusions 132 and/or holder 36 itself, and retaining holder 36 therein.

Figure 6:
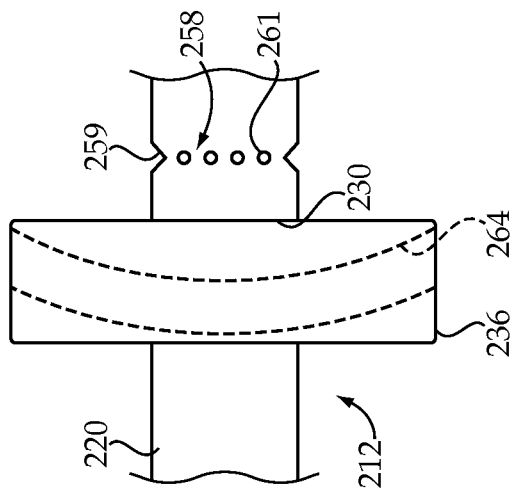
FIG. 6 is a top elevational view of a portion of a packaging system, according to yet another embodiment.

Referring to FIG. 6, there is shown another alternative embodiment of a packaging system 212 including a connector 220 and, a holder 236 positioned within a channel 230 formed in connector 220. In contrast to foregoing embodiments, in the FIG. 6 embodiment, a passage 264 defined by holder 236 has a generally arcuate shape, but an outer shape of holder 236 is not itself considered arcuate. Accordingly, holder 236, while not arcuate itself, could still be understood to define a circular arc segment by virtue of the shape of passage 264. System 212 also illustrates additional features relating to a break line 258 formed within connector 220. Break line 258 is formed in part by cut outs 259 arranged along sides of connector 220, and perforations 261 which pass vertically through connector 220. The features of break line 258 might be used in whole or in part in connection with the FIG. 6 embodiment, but also in connection with any of the other embodiments discussed herein.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A packaging system for medical devices comprising:
an elongate connector including a first and a second longitudinal end, and defining a latitudinal centerline located between the first and second longitudinal ends, and the elongate connector further including a lower surface, and an upper surface having a plurality of channels formed therein;
the plurality of channels including a first set of longitudinally spaced channels located on a first side of the latitudinal centerline, and a second set of longitudinally spaced channels located on a second side of the latitudinal centerline;
a first and a second tubular holder configured to form an assembly with an elongate medical device held in a coiled configuration by the first and second tubular holders opposed by an internal bias of the elongate medical device tending to uncoil the same; and
the first and second tubular holders each having shapes congruous with shapes of the plurality of channels, and being positionable within any combination of one of the first set of longitudinally spaced channels and one of the second set of longitudinally spaced channels, such that the elongate connector forms a bridge attaching the first and second tubular holders in the assembly with the elongate medical device.

2. The packaging system of claim 1 wherein the first set of longitudinally spaced channels each have a first channel shape, and the second set of longitudinally spaced channels each have a second channel shape substantially a mirror image of the first channel shape.

3. The packaging system of claim 2 wherein each of the first and second channel shapes includes an arcuate channel shape defining a circular arc opening toward the latitudinal centerline, and wherein the elongate connector defines a longitudinal axis bisecting each of the circular arcs in a projection plane.

4. The packaging system of claim 2 wherein each of the first and second tubular holders has an arcuate holder shape and a greater radial thickness, and wherein each of the plurality of channels has a lesser radial thickness, such that the first and second tubular holders are positionable therein via an interference fit.

5. The packaging system of claim 4 wherein each of the first and second tubular holders defines an axial thickness less than the greater radial thickness.

6. The packaging system of claim 2 wherein the elongate connector includes a first break line between two of the first set of longitudinally spaced channels, and a second break line between two of the second set of longitudinally spaced channels.

7. The packaging system of claim 6 wherein the elongate connector is formed of a material, and each of the first and second break lines is formed by at least one of a non-uniformity in a thickness of the material and a void in the material.

8. A medical device package comprising:
an elongate connector having a first and a second longitudinal end, a lower side, and an upper side having formed therein a first and a second channel positioned upon opposite sides of a latitudinal centerline located between the first and second longitudinal ends;
a first and a second tubular holder;
an elongate medical device held in a coiled configuration by the first and second tubular holders in opposition to an internal bias of the elongate medical device tending to uncoil the same; and
the first and second tubular holders being positioned within the first and second channels, respectively, such that the elongate connector forms a bridge attaching the first and second tubular holders.

9. The package of claim 8 wherein the first and second tubular holders are interference fitted into the first and second channels.

10. The package of claim 9 wherein the first channel has a first channel shape and the second channel has a second channel shape which is substantially a mirror image of the first channel shape, and wherein the first and second tubular holders each have a holder shape congruous with both of the first and second channel shapes.

11. The package of claim 10 wherein each of the first and second channel shapes includes an arcuate channel shape defining a circular arc, and wherein the elongate connector defines a longitudinal axis bisecting the circular arcs and bisecting the first and second tubular holders in a projection plane.

12. The package of claim 11 wherein the elongate connector further includes a third and a fourth channel formed in the upper side and positioned adjacent the first and second channels, respectively, and each of the third and fourth channels having a shape substantially identical to the shape of the adjacent first or second channel.

13. The package of claim 12 wherein the elongate connector includes a first break line between the first and third channels, and a second break line between the second and fourth channels.

14. The package of claim 11 wherein the holder shape includes an arcuate holder shape, and wherein each of the first and second tubular holders includes a greater radial thickness and a lesser axial thickness.

15. The package of claim 8 wherein the elongate medical device includes a wire guide having a proximal wire end protruding from the first holder, and a distal end wire protruding from the second holder.

16. The package of claim 15 further comprising a sterile pouch containing the elongate connector, the first and second tubular holders, and the elongate medical device.

17. A method of packaging an elongate medical device comprising the steps of:
coiling an elongate medical device against an internal bias of the elongate medical device tending to uncoil the same;
feeding the elongate medical device through a first and a second tubular holder during the step of coiling, such that the first and second tubular holders form an assembly with the elongate medical device in a coiled configuration opposed by the internal bias; and
positioning the first and second tubular holders within a first and a second channel, respectively, located upon opposite sides of a latitudinal centerline in an elongate connector, such that the elongate connector forms a bridge attaching the first and second tubular holders in the assembly with the elongate medical device.

18. The method of claim 17 wherein the step of positioning further includes interference fitting the first and second tubular holders into the first and second channels.

19. The method of claim 18 wherein the first and second channels are each one of a total of at least four longitudinally spaced channels having among them at least two different longitudinal spacings across the latitudinal centerline.

20. The method of claim 19 further comprising the steps of breaking off an end piece of the elongate connector wherein at least one of the longitudinally spaced channels is formed, and placing the assembly with the attached elongate connector within a packaging pouch.

* * * * *